United States Patent [19]
Gudas et al.

[11] Patent Number: 6,150,421
[45] Date of Patent: Nov. 21, 2000

[54] TREATMENT OF ESTROGEN-RECEPTOR POSITIVE BREAST CANCER AND ESTROGEN-RECEPTOR NEGATIVE BREAST CANCER WITH RETINOID WITH $CH_2OH$ AT THE SIDE CHAIN TERMINAL POSITION

[75] Inventors: Lorraine Gudas; Fadila Derguini, both of New York, N.Y.

[73] Assignee: Cornell Research Foundation, Inc., Ithaca, N.Y.

[21] Appl. No.: 09/088,770

[22] Filed: Jun. 2, 1998

Related U.S. Application Data

[63] Continuation-in-part of application No. 08/371,535, Jan. 11, 1995, Pat. No. 5,786,391.
[60] Provisional application No. 60/050,090, Jun. 18, 1997.

[51] Int. Cl.$^7$ .............................. A61K 31/12; A61K 31/11
[52] U.S. Cl. ........................ 514/690; 514/723; 514/729
[58] Field of Search .................................. 514/690, 723, 514/729

[56] References Cited

U.S. PATENT DOCUMENTS

| | | | |
|---|---|---|---|
| 3,931,257 | 1/1976 | Pawson | 554/218 |
| 5,124,083 | 6/1992 | Shealy | 514/529 |
| 5,786,391 | 7/1998 | Gudas et al. | 514/690 |
| 5,962,534 | 10/1999 | Gudas et al. | 514/690 |

OTHER PUBLICATIONS

Sheikh et al., "Why are estrogen–receptor–negative breast cancers more aggressive than estrogen–receptor–positive breast cancers?", Invasion and Metastasis, vol. 14/1–6: 329–336, 1994.

Fitzgerald et al., "Retinoic acid receptor alpha expression correlates with retinoid–induced growth inhibition of human breast cancer cells regardless of estrogen receptor status.", Cancer Research, vol. 57(13): 2642–2650, 1997.

Achkar, C. C., et al., Proc. Nat'l Acad. Sci.USA, vol. 93, pp. 4879–4884, May 1996.

Chen, A. A., et al., Cancer Research 57, 4642–4651 (Oct. 15, 1997).

Hong, W. K., et al., "Retinoids and Human Cancer" in The Retinoids, Biology, Chemistry and Medicine, $2^{nd}$ edition, edited by Sporn, M. B., et al., Raven Press Ltd., New York, 1994, pp. 597–630.

*Primary Examiner*—Howard C. Lee

[57] ABSTRACT

Certain retinoids with $CH_2OH$ at the side chain terminal position, preferably 4-oxoretinol, inhibit growth of estrogen-receptor positive and estrogen-receptor negative breast cancer tumor cell lines and have utility for adjuvant therapy and treatment of metastatic disease.

14 Claims, 2 Drawing Sheets

T47D

MDA-MB-231

MDA-MB-468

TREATMENT OF ESTROGEN-RECEPTOR POSITIVE BREAST CANCER AND ESTROGEN-RECEPTOR NEGATIVE BREAST CANCER WITH RETINOID WITH CH₂OH AT THE SIDE CHAIN TERMINAL POSITION

CROSS-REFERENCE TO RELATED APPLICATIONS

This application claims the benefit of U.S. Provisional Application No. 60/050,090, filed Jun. 18, 1997 and is a continuation-in-part of Application Ser. No. 08/371,535, filed Jan. 11, 1995, now U.S. Pat. No. 5,786,391.

The invention was made at least in part with United States Government support under grant number RO1CA43796 and under grant number RO1GM47599, both from the National Institutes of Health. The United States Government has certain rights in the invention.

TECHNICAL FIELD

This invention is directed to treating estrogen-receptor positive breast cancer and estrogen-receptor negative breast cancer in patients afflicted with these conditions.

BACKGROUND OF THE INVENTION

Breast cancer tumors are classified as either estrogen-receptor positive (ER+) or estrogen-receptor negative (ER−). Classification procedures are well-known and include measurement of intracellular receptor protein by either a steroid-binding assay or by immunochemical assay or by measuring mRNA corresponding to said protein using Northern blot analysis. The term "estrogen-receptor positive breast cancer" is used herein to denote the disorder of those patients who were determined to have estrogen-receptor positive (ER+) breast cancer tumors prior to primary treatment. The term "estrogen-receptor negative breast cancer" is used herein to denote the disorder of those patients who were determined to have estrogen-receptor negative (ER−) breast cancer tumors prior to primary treatment.

Primary treatment in the case of those determined to have estrogen-receptor positive breast cancer tumors or estrogen-receptor negative breast cancer tumors is mastectomy or breast conserving surgery (lumpectomy, tylectomy, wide excision, partial mastectomy, or quadrantectomy) plus radiation therapy.

Adjuvant systemic therapy is begun soon after primary therapy to delay recurrence and/or to prolong survival. One kind of adjuvant systemic therapy is adjuvant chemotherapy, e.g., using a combination regimen of cyclophosphamide, methotrexate and 5-fluorouracil, e.g., for four to 24 months. Another kind of adjuvant systemic therapy is adjuvant tamoxifen therapy given for two to five years. Adjuvant chemotherapy is given routinely to all premenopausal, node-positive patients. Adjuvant tamoxifen therapy is given routinely to post-menopausal women who are node-positive and have estrogen-receptor positive tumors.

Patients with metastatic disease are treated with endocrine therapy or chemotherapy or in some cases with radiation therapy to palliate symptoms.

The method of the invention offers an alternative or supplement to chemotherapy and tamoxifen therapy for adjuvant therapy and for the first time offers an adjuvant therapy treatment different from normal relatively toxic chemotherapy for those with estrogen-receptor negative breast cancer. Moreover, the method of the invention offers an alternative or supplement to chemotherapy, endocrine therapy and radiation therapy in the treatment of metastatic disease.

SUMMARY OF THE INVENTION

It has been discovered herein that administration of retinoids as described hereinafter to those with estrogen-receptor positive breast cancer and to those with estrogen-receptor negative breast cancer inhibits breast cancer cell growth and metastatic cell growth.

One method herein is directed to treating estrogen-receptor positive breast cancer in a patient afflicted with this condition and comprises administering to said patient as adjuvant therapy a therapeutically effective amount, i.e., a breast cancer cell growth inhibiting amount of a retinoid as described hereinafter.

Another method herein is directed to treating estrogen-receptor negative breast cancer in a patient afflicted with this condition and comprises administering to said patient as adjuvant therapy a therapeutically effective amount, i.e., a breast cancer cell growth inhibiting amount of a retinoid as described hereinafter.

Still another method herein is directed to treating estrogen-receptor positive breast cancer that has metastasized in a patient affected with this condition and comprises administering to said patient a therapeutically effective amount, i.e., a metastatic cell growth inhibiting amount of a retinoid as described hereinafter.

Still another method herein is directed to treating estrogen-receptor negative breast cancer that has metastasized in a patient affected with this condition and comprises administering to said patient a therapeutically effective amount, i.e., a metastatic cell growth inhibiting amount of a retinoid as described hereinafter.

The retinoids for use in the methods herein have the structure

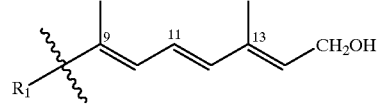

wherein the configuration at the 7-, 9-, 11- and 13-position double bonds is independently Z or E and wherein $R_1$ is selected from the group consisting of (I)

(a)

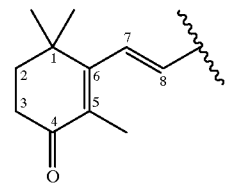

wherein the keto group at the 4-position is free or protected; and (b)

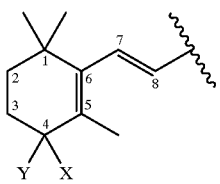

(II)

wherein X is selected from the group consisting of hydrogen and $C_{1-6}$-alkyl and wherein Y is selected from the group consisting of hydroxy and $C_{1-6}$-alkoxyl, and wherein the absolute configuration at the 4-position is independently R or S or a mixture R and S.

Preferred retinoids for use herein include 4-oxoretinol and 4-hydroxyretinol.

The terms "4-oxoretinol" and "4-hydroxyretinol" are used herein to mean the all-trans forms as well as isomeric forms of these including the 7-cis, 9-cis, 11-cis and 13-cis isomers, and the term "4-hydroxyretinol" is used herein to mean the (4R) or (4S) enantiomeric forms or a mixture of the (4R) and (4S) enantiomeric forms. The all-trans forms are preferred. The most preferred retinoid for use herein is all-trans-4-oxoretinol.

DETAILED DESCRIPTION

Figure 1A:
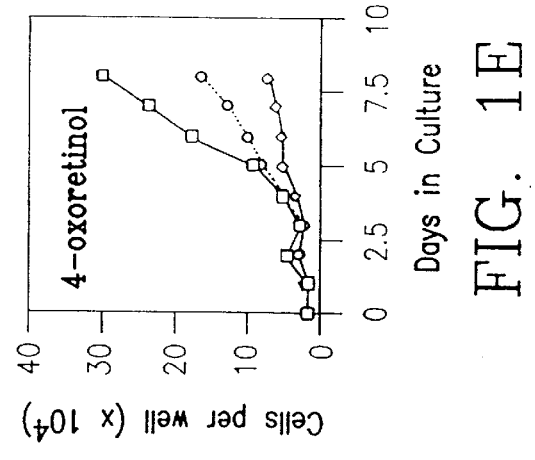
FIGS. 1A, 1B, 1C, 1D, 1E, and 1F depict graphically the effects determined in Example I for retinoic acid, 4-(hydroxyphenyl)retinamide, and 4-oxoretinol on the growth of MCF-7 and MDA-MB-231 cell lines.

Pharmaceutically pure all-trans-4-oxoretinol and pharmaceutically pure all-trans-4-hydroxyretinol are readily obtained by inducing differentiation in F9 mouse teratocarcinoma stem cells, an established widely used line, from a murine tumor, available from the American Type Culture Collection under Accession No. ATCC CRL 1720, with retinoic acid, whereby the endogenous retinol (Vitamin A) is metabolized into many derivatives in the differentiated cells, including all-trans-4-oxoretinol and all-trans-4-hydroxyretinol, and isolating the all-trans-4-oxoretinol and all-trans-4-hydroxyretinol in pharmaceutically pure form. This can be carried out to obtain pharmaceutically pure all-trans-4-oxoretinol by culturing the F9 stem cells in the presence of retinoic acid (to induce differentiation), and extracting using the procedure of McClean, S. W., et al., Clin. Chem. 284, 693–696 (1982) and isolating pharmaceutically pure all-trans-4-oxoretinol.

The compound all-trans-4-oxoretinol can also be prepared according to several known procedures as follows: A first method involves selective $NaBH_4$ reduction of 4-oxoretinal, obtained by $MnO_2$ oxidation of 4-hydroxy-retinal. See Boehm, M F., et al., J. Am. Chem. Soc. 112, 7779–7782 (1990). The latter can be prepared from commercially available all-trans-retinal. See Henbest, H. B., et al., J. Am. Chem. Soc. 4909–4912 (1957); Reedy, A. J., French Patent 1,484,573 abstracted in Chem. Abst. 68, 29903m (1968); Surmatis, J. D., U.S. Pat. No. 3,311,656; and Renk, G., et al., Photochem. Photobiol. 33, 489–494 (1981). A second method involves the synthesis of 4-oxo-retinal by direct oxidation of retinol or retinal by $MnO_2$. See Henbest, H. B., et al., J. Chem. Soc. 4909–4912 (1957) and Williams, T. C., et al., Biochemistry 30, 2976–2988 (1991). A third method involves hydrolysis of 4-oxo-retinyl acetate prepared from commercially available retinyl acetate. See Henbest, H. B., et al., J. Chem. Soc. 4909–4912 (1957).

Racemic all-trans-4-hydroxy-retinol can be synthesized by $NaBH_4$ reduction of 4-hydroxy, or 4-oxo-retinal obtained as described in Henbest, H. B., et al, J. Chem. Soc. (1957). 4909–4912; Reedy, A. J., et al, French Patent 1,484,573 (Chem. Abstr. 68: 29903m (1968); Surmatis, J. D. U.S. Pat. No. 3,311,656; Renk, G., et al, Photochem. Photobiol. 33, 489–494 (1981; and Williams, T. C., et al, Biochemistry 30, 2976–2988 (1991).

All-trans (4S)-4-hydroxyretinol can be prepared starting with (4S)-4-hydroxy-β-ionone obtained as described in Haag, A., et al, Helv. Chim. Acta 63, 10–15 (1980). Elongation of the side chain is achieved by conventional Horner-Emmons reactions as described in Haag, A., et al, Helv. Chim. Acta 65: 1795–1803 (1982); Katsuta, Y., et al, Tetrahedron Lett. 35: 905–908 (1994); and Katsuta, Y., et al, J. Org. Chem. 59, 6917–6921 (1994).

All-trans (4R)-4-hydroxyretinol can be obtained similarly, starting with (4R)-4-hydroxy-β-ionone obtained as described in Haag, A., et al, Helv. Chim. Acta 63, 10–15 (1980).

Racemic 4-hydroxyretinol can be obtained similarly starting from racemic 4-hydroxy-β-ionone as described in Haag, A., et al, Helv. Chim. Acta 63, 10–15 (1980). The synthesis of 4-hydroxylated retinols from 4-hydroxylated β-ionone leads to mixture of isomers which can be separated as described in Katsuta, Y., J. Org. Chem. 59, 6917–6921 (1994). Furthermore mixtures enriched with Z-isomers can be prepared employing elongation procedures using trimethylsilylacetone tert-butylamine as described in Croteau, A., J. Tetrahedron Lett. 24, 2481–2484 (1983) or bis (trifluoroethyl)-2-methyl-3-cyano-2-propenyl phosphonate as described in Van Den Tempel, P. J., et al, Tetrahedron 22, 233–299 (1966) and Trehan, A., et al, Tetrahedron 46, 3769–3780 (1990).

Others of the retinoids herein are prepared following retinoid synthetic procedures well-known to those skilled in the art. See, for example, Dawson, M. I., et al, Editors, Chemistry and Biology of Synthetic Retinoids, CRC Press Inc., (1990) and Sporn, M. B., et al, Eds., The Retinoids, Vol. 1, Academic Press, Inc., (1984), which are incorporated herein by reference.

For all the methods of treatment described above, administration is carried out by methods well-known to those skilled in the art which include but are not limited to, administration orally and administration parenterally including intravenously and by intramuscular administration, and administration transdermally, e.g., using a patch on the skin, and administration may be effected continuously or intermittently such that the amount of retinoid in the patient is effective to obtain benefit.

The retinoid is readily administered as a composition including a pharmaceutically acceptable carrier. Compositions for oral administration may be, for example, in capsule or pill form and comprise a therapeutically effective amount of retinoid herein and pharmaceutically acceptable carrier, e.g., a pharmaceutically acceptable excipient such as calcium carbonate, sodium carbonate, lactose or talc. Compositions for parenteral administration of retinoid herein and pharmaceutically acceptable carrier such as sterile water or physiological saline, and lysosome delivery systems can be used to accommodate for lack of solubility (all-trans-4-oxoretinol is slightly soluble in water). For transdermal administration from a patch, the retinoid herein can be formed into a dispensing layer which is positioned between adhesive layers on a backing film.

The dosages, i.e., the therapeutically effective amounts for all the treatment methods herein for the retinoids herein are, for example, 5 to 5,000 mg per square meter of the body per day (0.1–100 mg/kg body weight/day). preferably 50 to 200 mg per square meter of the body per day, for oral administration; 5 to 5,000 mg per square meter of the body per day, preferably 20 to 200 mg per square meter of the body per day for parenteral administration and 5 to 5,000 mg per square meter of the body per day, preferably 20 to 200 mg per square meter of the body per day for transdermal administration. For adjuvant therapy administration is continued for two to five years. In the case of metastasized breast cancer, treatment is preferably continued until no further response is seen.

The efficacy of 4-oxoretinol in inhibiting the growth of estrogen-receptor positive breast cancer cell lines and in inhibiting the growth of estrogen-receptor negative breast cancer cell lines is shown in a manuscript titled "Breast Cancer Cells and Normal Mammary Epithelial Cells: Retinol Metabolism and Growth Inhibition By the Retinol Metabolite 4-Oxoretinol", which published as Chen, A. C., et al., Cancer Research 57, 4642–4651 (Oct. 17, 1997), which is incorporated herein by reference.

The U.S. application Ser. Nos. 60/050090 and 08/371535 are incorporated herein by reference.

The invention is illustrated in the following specific examples.

EXAMPLE I

Cells initially at a concentration of $1.0 \times 10^4$/well were grown at 37° C. in Dulbecco's modified Eagle's medium (Catalog No. 10-331-22, ICN Biomedicals, Inc., Costa Mesa, Calif.) supplemented with 10% heat inactivated fetal calf serum, 2 mM glutamine and 5 $\mu$g/ml insulin in 5% $CO_2$.

In a first experiment, the cells used were MCF-7 estrogen-receptor positive human breast cancer cell line (obtained from the American Type Culture Collection, Rockville, Md., under Accession No. HTB 22) and MDA-MB-231 estrogen-receptor negative human breast cancer cell line (obtained from the American Type Culture Collection, Rockville, Md., under Accession No. HTB 26). Cells were plated either without drug (control) or in the presence of all-trans-oxoretinol (4-oxoretinol), all-trans-retinoic acid (RA) or N-(4-hydroxyphenyl)retinamide (4-HPR). In all the experiments, one part of ethanol was included per 1,000 parts of medium. The drugs were included in amounts of 1 $\mu$M and 0.1 $\mu$M based on the medium. Culturing was carried out for 10 days. On days 0, 1, 2, 3, 4, 5, 6, 7 and 8 cells were trypsinized and counted using a Coulter Counter. The results are plotted in number of cells ($\times 10^4$) per well (y axis) versus days in culture (x axis) and are shown in FIGS. 1A–1F. In FIGS. 1A–1F, the open squares define graphs for the control experiment, the open circles define graphs for drug used in amount of 0.1 $\mu$M and the open diamonds define graphs for drug used in amount of 1 $\mu$M. Each point in FIGS. 1A–1F is the mean of quadruplicate samples. In FIGS. 1A through 1F, the bars represent standard deviation, and no bar represents a standard deviation of less than 0.01.

Figure 2A:
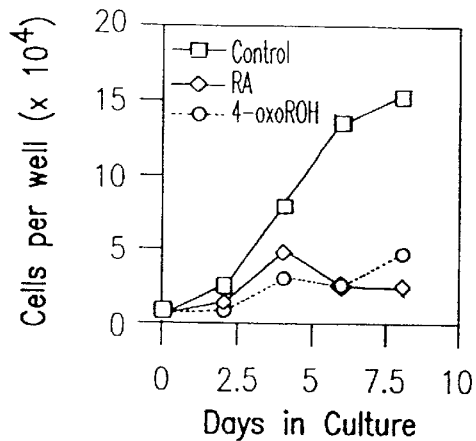
FIGS. 2A, 2B and 2C depict graphically the effects determined in Example I for retinoic acid and 4-oxoretinol on the growth of T47D, MDA-MB-231, and MDA-MB-468 cell lines.
Figure 2B:
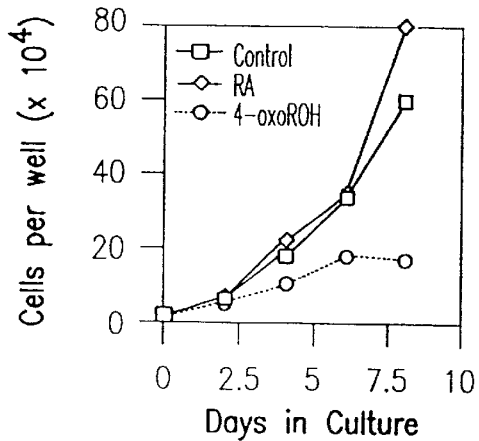
Figure 2C:
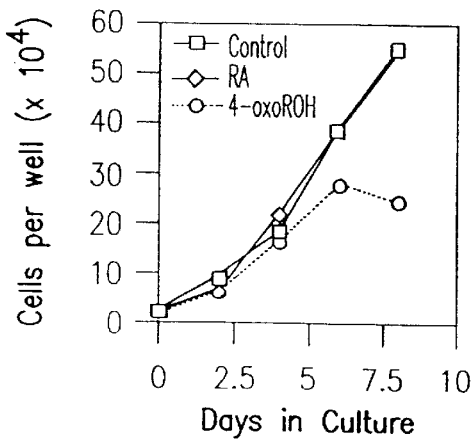

A second experiment was carried out similar to the first experiment except that the cell lines used were T47D estrogen-receptor positive human breast cancer cell line (obtained from the American Type Culture Collection, Rockville, Md., under Accession No. HTB 133), MDA-MB-231 estrogen-receptor negative human breast cancer cell line (obtained from the American Type Culture Collection, Rockville, Md., under Accession No. HTB 26) and MDA-MB-468 estrogen negative human breast cancer cell line (obtained from the American Type Culture Collection, Rockville, Md., under Accession No. HTB 132) and the drugs were all-trans-retinoic acid (RA) and all-trans-4-oxoretinol (4-oxoROH) Cells were plated either without drug (control) or in the presence of 1 $\mu$M drug (concentration based on the medium) and cells were counted on days 0, 2, 4, 6 and 8. Results are shown in FIGS. 2A–2C wherein the open squares define graphs for control experiments, the open diamonds define graphs for experiments where all-trans-retinoic acid was the drug and the open circles define graphs for experiments where all-trans-4-oxoretinol was the drug.

Figure 1C:
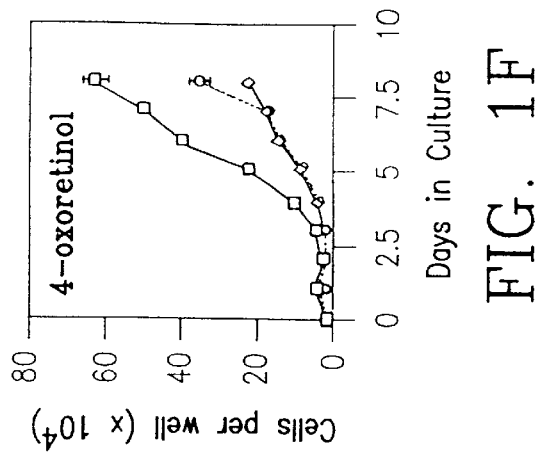
Figure 1E:
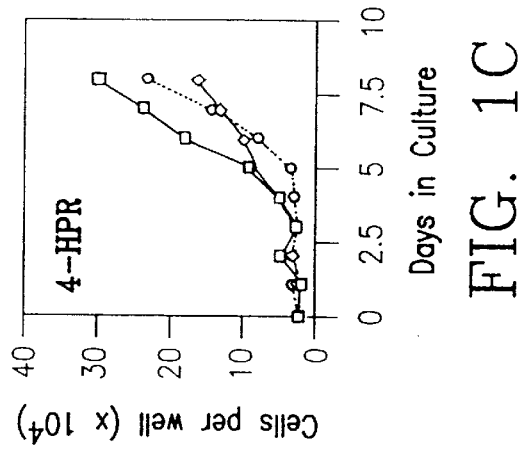
Figure 1B:
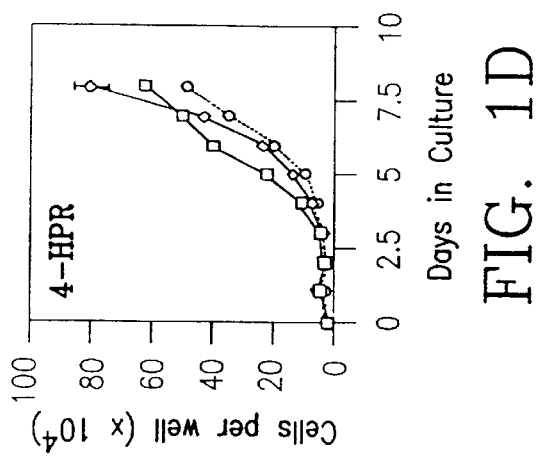
Figure 1D:
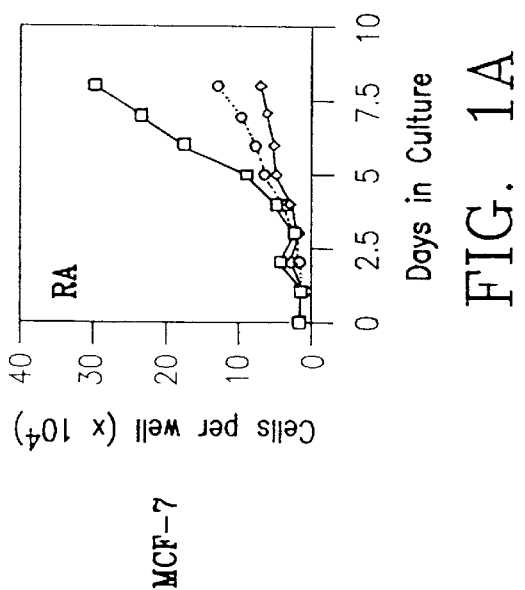
Figure 1F:
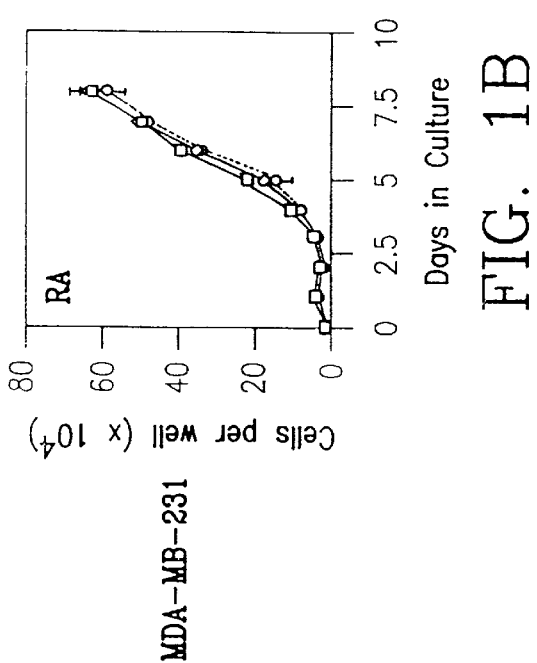

All three drugs exhibited growth inhibiting activity in the estrogen-receptor positive MCF-7 cancer cell line; both retinoic acid and 4-oxoretinol were superior to 4-HPR with respect to growth inhibition (FIGS. 1A, 1C, 1E). In the estrogen-receptor negative MDA-MB-231 cell line, neither retinoic acid nor 4-HPR were growth inhibitory at the concentrations used; however, 4-oxoretinol at 1 $\mu$M inhibited growth of MDA-MB-231 cells by about 65% (FIGS. 1B, 1D, 1F and 2B). In the estrogen-receptor positive T47D cell line, both retinoic acid and 4-oxoretinol inhibited cell growth (FIG. 2A). In the estrogen-receptor negative MDA-MB-468 cell line, 4-oxoretinol, but not retinoic acid, inhibited growth (FIG. 2C). Thus 4-oxoretinol is shown to be superior to both retinoic acid and 4-HPR in inhibiting growth of estrogen-receptor negative breast cancer cells.

In similar experiments on MCF-7 cells and or MDA-MB-231 cells with 4-oxoretinaldehyde, growth arrest was substantially less than was obtained with 4-oxoretinol.

EXAMPLE II

A patient with estrogen-receptor negative breast cancer is treated with all-trans-4-oxoretinol for adjuvant therapy at oral doses of 100 mg/square meter of body surface per day for five years after a mastectomy. Recurrence of breast cancer does not occur.

Similar results are obtained in Example II when administration is by intramuscular injection or from patch on skin.

EXAMPLE III

A patient with estrogen-receptor positive breast cancer is treated with all-trans-4-oxoretinol for adjuvant therapy at oral doses of 125 mg/square meter of body surface per day for three years after a mastectomy. Recurrence of breast cancer does not occur.

Similar results are obtained in Example III when administration is by intramuscular injection or from a patch on skin.

EXAMPLE IV

Breast cancer is determined to have metastasized to lung and liver three years after a mastectomy is performed on a patient with estrogen-receptor negative breast cancer. The patient is treated with oral doses of all-trans-4-oxoretinol of 150 mg/square meter of body surface per day. A reduced tumor burden is noted.

Similar results are obtained in Example IV when administration is by intramuscular injection or from a patch on skin.

EXAMPLE V

Breast cancer is determined to have metastasized to bone nine years after a mastectomy is performed on a patient with estrogen-receptor positive breast cancer. The patient is treated with oral doses of all-trans-4-oxoretinol of 200 mg/square meter of body surface per day. A reduced tumor burden is noted.

Similar results are obtained in Example V when administration is by intramuscular injection or from a patch on skin.

EXAMPLE VI

Similar results to those obtained in Examples II–V are obtained when all-trans-4-hydroxyretinol (P or S enantiomer) is substituted for the all-trans-4-oxoretinol or when other retinoids herein are substituted for the all-trans-4-oxoretinol.

Many variations of the above will be obvious to those skilled in the art. Thus, the invention is defined by the claims.

What is claimed is:

1. A method of treating estrogen-receptor positive breast cancer in a patient afflicted with this condition, comprising administering to said patient as adjuvant therapy a therapeutically effective amount of a retinoid having the structure

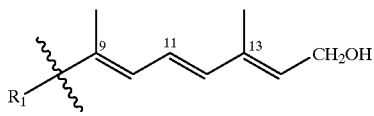

(I)

wherein the configuration at the 7-, 9-, 11- and 13-position double bonds is independently Z or E and wherein $R_1$ is selected from the group consisting of (a)

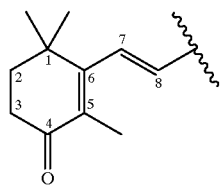

wherein the keto group at the 4-position is free or protected; and (II)

(b)

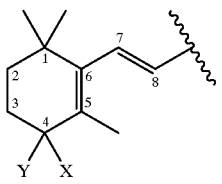

wherein X is selected from the group consisting of hydrogen and $C_{1-6}$-alkyl and wherein Y is selected from the group consisting of hydroxy and $C_{1-6}$-alkoxyl, and wherein the absolute configuration at the 4-position is independently R or S, or a mixture of R and S.

2. The method of claim 1, wherein the retinoid is 4-oxoretinol.

3. The method of claim 2, wherein the 4-oxoretinol is all-trans-4-oxoretinol.

4. The method of claim 1, wherein the retinoid is 4-hydroxyretinol.

5. The method of claim 4, wherein the 4-hydroxyretinol is all-trans-4-hydroxyretinol.

6. A method of treating estrogen-receptor negative breast cancer in a patient affected with this condition comprising administering to said patient as adjuvant therapy a therapeutically effective amount of 4-oxoretinol.

7. The method of claim 6, wherein the 4-oxoretinol is all-trans-4-oxoretinol.

8. A method of treating estrogen-receptor positive breast cancer that has metastasized in a patient affected with this condition, comprising administering to said patient a therapeutically effective amount of a retinoid having the structure

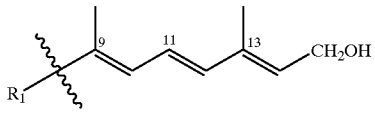

wherein the configuration at the 7-, 9-, 11- and 13-position double bonds is independently Z or E and wherein $R_1$ is selected from the group consisting of (I)

(a)

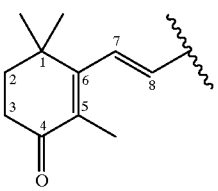

wherein the keto group at the 4-position is free or protected; and (II)

(b)

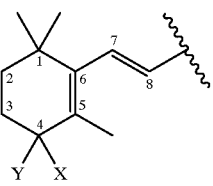

wherein X is selected from the group consisting of hydrogen and $C_{1-6}$-alkyl and wherein Y is selected from the group consisting of hydroxy and $C_{1-6}$-alkoxyl, and wherein the absolute configuration at the 4-position is independently R or S, or a mixture of R and S.

9. The method of claim 8, wherein the retinoid is 4-oxoretinol.

10. The method of claim 9, wherein the 4-oxoretinol is all-trans-4-oxoretinol.

11. The method of claim 8, wherein the retinoid is 4-hydroxyretinol.

12. The method of claim 11, wherein the 4-hydroxyretinol is all-trans-4-hydroxyretinol.

13. A method of treating estrogen-receptor negative breast cancer that has metastasized in a patient affected with this condition, comprising administering to said patient a therapeutically effective amount of 4-oxoretinol.

14. The method of claim 13, wherein the 4-oxoretinol is all-trans-4-oxoretinol.

* * * * *